(12) United States Patent
Wessman et al.

(10) Patent No.: US 6,231,589 B1
(45) Date of Patent: May 15, 2001

(54) BODY VESSEL FILTER

(75) Inventors: Bradley John Wessman, Maple Grove, MN (US); Bart Lewis Dolmatch, Hunting Valley, OH (US); Brian Lee Dukart, Brooklyn Park, MN (US)

(73) Assignee: Microvena Corporation, White Bear Lake, MN (US)

( * ) Notice: Subject to any disclaimer, the term of this patent is extended or adjusted under 35 U.S.C. 154(b) by 0 days.

(21) Appl. No.: 09/273,396

(22) Filed: Mar. 22, 1999

(51) Int. Cl.$^7$ .................................................. A61M 29/00
(52) U.S. Cl. ............................................................ 606/200
(58) Field of Search .................................... 606/200, 198, 606/191; 604/53, 104, 105, 106, 107, 108

(56) References Cited

U.S. PATENT DOCUMENTS

| | | |
|---|---|---|
| 3,540,431 | 11/1970 | Mobin-Uddin . |
| 3,952,747 | 4/1976 | Kimmell, Jr. . |
| 4,425,908 | 1/1984 | Simon . |
| 4,430,081 | 2/1984 | Timmermans . |
| 4,494,531 | 1/1985 | Gianturco . |
| 4,512,338 | 4/1985 | Balko et al. . |
| 4,619,246 | 10/1986 | Molgaard-Nielsen et al. . |
| 4,643,184 | 2/1987 | Mobin-Uddin . |
| 4,665,906 | 5/1987 | Jervis . |
| 4,688,553 | 8/1987 | Metals . |
| 4,727,873 | 3/1988 | Mobin-Uddin . |
| 4,781,177 | 11/1988 | Lebigot . |
| 4,817,600 | 4/1989 | Herms et al. . |
| 4,832,055 | 5/1989 | Palestrant . |
| 4,873,978 | 10/1989 | Ginsburg . |
| 4,969,891 | 11/1990 | Gewertz . |
| 4,990,156 | 2/1991 | Lefebvre . |
| 4,998,539 | 3/1991 | Delsanti . |
| 5,035,706 | 7/1991 | Giantureo et al. . |
| 5,059,205 | 10/1991 | El-Nounou et al. . |
| 5,067,957 | 11/1991 | Jervis . |
| 5,071,407 | 12/1991 | Termin et al. . |

(List continued on next page.)

FOREIGN PATENT DOCUMENTS

| | | |
|---|---|---|
| WO96/01591 | 1/1996 | (WO) . |
| WO96/12448 | 5/1996 | (WO) . |

OTHER PUBLICATIONS

Interventional Radiology, vol. 1, Third Edition (© 1997) by Wilfrido R. Castaneda–Zuniga, M.D., M.Sc., pp. 854–896; 941–961.

Comparative in Vitro Evaluation of the Nitinol Interior Vena Cava Filter, by Aubrey M. Palestrant, M.D., Martin Prince, B.S., and Morris Simon, M. D., Radiology 145: pp. 351–355, Nov., 1982.

Primary Examiner—Michael Buiz
Assistant Examiner—Anthony S. King
(74) Attorney, Agent, or Firm—Fredrikson & Byron

(57) ABSTRACT

A catheter-deliverable filter assembly deployable in a vessel of the body in alternatively a temporary configuration enabling the filter to be removed from the vessel or a permanent configuration, and a method for its use. The filter assembly comprises an elongated support carrying spaced along its length a filter element and a anchoring element with the filter element being spaced distally from the anchoring element. Each element comprises a core mounted to the elongated support and a plurality of flexible, resilient wires extending distally from the core, the wires having proximal portions attached at one end to the core and distal portions. The wires of the anchoring element include gripping elements for gripping the walls of a vessel. The wires are so configured as to support the apices of the filter and anchoring elements substantially in the center of the vessel. The filter assembly may include a hollow flexible tether releasably attached to the proximal end of the elongated support and having a distal end portion within which are resiliently confined the wires of the anchoring element when the filter element alone is deployed.

13 Claims, 5 Drawing Sheets

U.S. PATENT DOCUMENTS

| | | | |
|---|---|---|---|
| 5,108,418 | | 4/1992 | Lefebvre . |
| 5,133,733 | | 7/1992 | Rasmussen et al. . |
| 5,147,379 | | 9/1992 | Sabbaghian et al. . |
| 5,152,777 | | 10/1992 | Goldberg et al. . |
| 5,190,546 | | 3/1993 | Jervis . |
| 5,234,458 | | 8/1993 | Metals . |
| 5,242,462 | * | 9/1993 | El-Nounou et al. .................. 606/200 |
| 5,282,824 | | 2/1994 | Gianturco . |
| 5,324,304 | | 6/1994 | Rasmussen . |
| 5,329,942 | | 7/1994 | Gunther et al. . |
| 5,344,427 | * | 9/1994 | Cottenceau et al. .................. 606/200 |
| 5,370,657 | * | 12/1994 | Irie ....................................... 606/200 |
| 5,397,310 | | 3/1995 | Chu et al. . |
| 5,415,630 | * | 5/1995 | Gory et al. ............................ 604/53 |
| 5,417,708 | | 5/1995 | Hall et al. . |
| 5,421,832 | | 6/1995 | Lefebvre . |
| 5,531,716 | | 7/1996 | Luzio et al. . |
| 5,531,735 | | 7/1996 | Thompson . |
| 5,531,788 | | 7/1996 | Dibie et al. . |
| 5,601,595 | * | 2/1997 | Smith .................................... 606/200 |
| 5,603,731 | | 2/1997 | Whitney . |
| 5,626,605 | * | 5/1997 | Irie et al. .............................. 606/200 |
| 5,634,942 | * | 6/1997 | Chevillon et al. ........................ 623/1 |
| 5,669,933 | | 9/1997 | Simon et al. . |
| 5,720,764 | | 2/1998 | Naderlinger . |
| 5,725,550 | * | 3/1998 | Nadal .................................... 606/200 |
| 5,746,767 | * | 5/1998 | Smith .................................... 606/200 |
| 5,776,162 | | 7/1998 | Kleshiski . |
| 5,800,457 | * | 9/1998 | Gelbfish ............................... 606/200 |
| 5,836,969 | | 11/1998 | Kim et al. . |

* cited by examiner

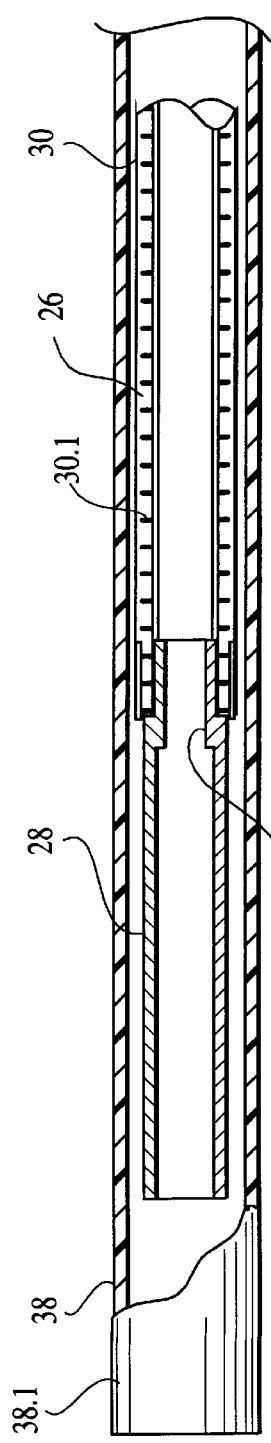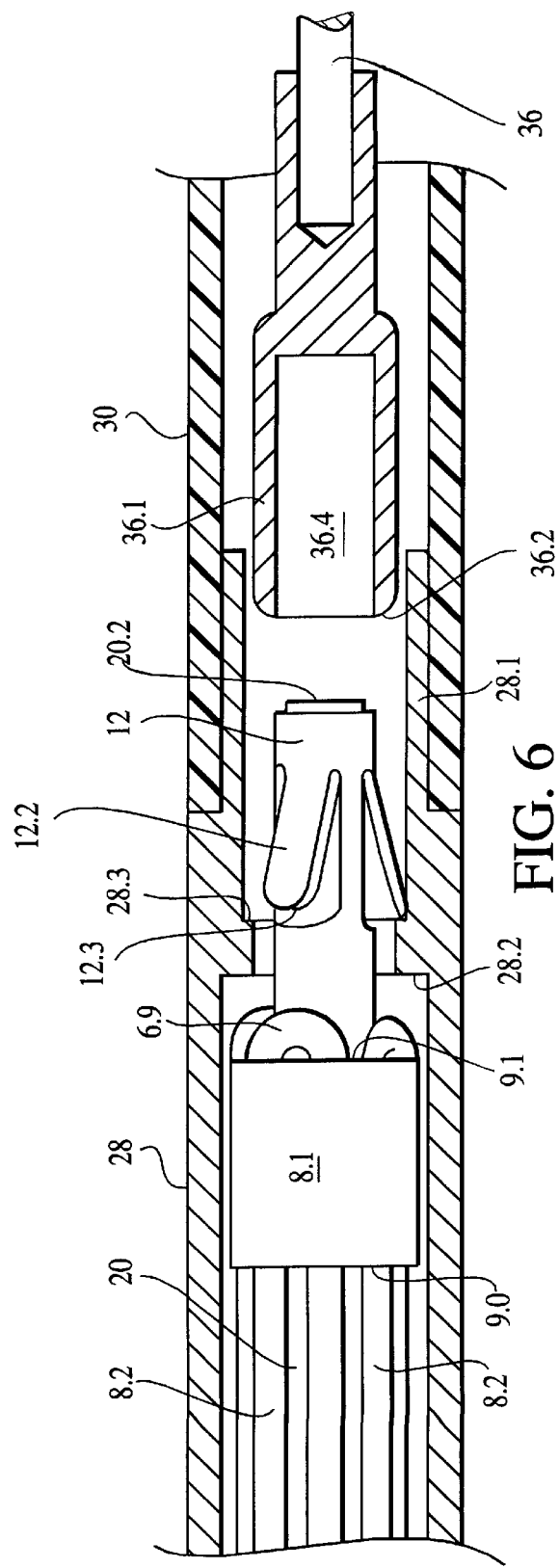

BODY VESSEL FILTER

BACKGROUND OF THE INVENTION

Pulmonary embolism, in which emboli from any of various regions of the vascular system pass into the lungs, accounts for thousands of deaths each year in the United States. Blood clots from the lower extremities are commonly carried to the heart through the inferior vena cava, and thence to the lungs.

Many patients with documented pulmonary embolism can be treated with anti-coagulants to prevent further formation of thrombi, but there are situations in which mechanical interruption of the inferior vena cava is the preferred method to prevent pulmonary embolism. To prevent blood clots from passing upwardly through the inferior vena cava, it has been suggested to place filters in the vena cava which filter out blood clots. An excellent but early description of vena cava filters is found in Palestrant, Aubrey, M, et al. *Comparative In Vitro Evaluation of the Nitinol Inferior Vena Cava Filter*, Radiology 145:351–355, November, 1982. A more recent treatment of the subject of vena cava filters is found in *Interventional Radiology*, $3^{rd}$ Edition, Castaeda-Zuniga, Wilfredo R., ed., Williams & Wilkins, Baltimore, pp 854–896 (1997). Various filters are disclosed in Lebigot, U.S. Pat. No. 4,781,177, Simon, et al., U.S. Pat. No. 5,669,933 and Maderlinger, U.S. Pat. No. 5,720,764. Reference may be made also to Rasmussen, et al., U.S. Pat. No. 5,133,733, LeFebvre, U.S. Pat. No. 5,108,418, Goldberg, et al. U.S. Pat. No. 5,152,777 and El-Nounou, et al. U.S. Pat. No. 5,242,462.

In general, vena cava filters are introduced into the vasculature through a puncture or an incision in a major vessel such as the internal jugular vein and the filter, elastically restrained in a delivery catheter, is passed from the jugular vein through the right atrium of the heart and into the inferior vena cava whereupon the filter is mechanically expelled from the catheter and expands into contact with the lumen. Various hook-like projections have been suggested for use in holding the filter in place once the delivery catheter has been withdrawn. When a filter using hooks, barbs and the like to retain it in place permanently is thus to be removed, surgical intervention is usually required.

Temporary introduction of a vena cava filter may be desired to provide rapid protection against pulmonary embolism, but as the condition producing blood clots is successfully treated, it may be desired to remove the filter from the vena cava. Vena cava filters commonly include a hub or central portion from which radiate outwardly a plurality of wires, sometimes in a woven configuration, the wires serving to filter clots from blood flowing through the vein. It is not uncommon for the central portion of the filter element, which is to be near the center of the lumen, to have the greatest efficiency, that is, to have wires that are closest together to thus produce smaller openings through which blood flows. The screen openings often become larger toward the walls of the vein. For good results, it is desired that the center of the filter remain near the center of the vessel, but often this is not easily controlled and the center of the filter may tilt to one side or the other of the lumen, thus exposing the less efficient areas of the filter to blood flow at the center of the lumen and reducing filtering efficiency.

Also, it is sometimes difficult to visualize with accuracy the effectiveness of a vena cava filter in filtering out blood clots. Commonly, an imaging or contrast medium such as Hipaque® (a product of Winthrop Pharmaceutical) or Conray® (a product of Mallinckrodt) may be injected upstream from the filter (that is, inferior to the filter in the vena cava) in the course of obtaining a vena cavogram, but the contrast liquid often becomes diluted in the blood stream as it reaches the filter, preventing precise visualization of blood clots in the filter. Moreover, to obtain a good vena cavogram, a large volume, e.g., 30 cc, of a contrast medium must be rapidly injected, and this procedure often is done with the aid of a diagnostic catheter.

Although, as thus described, a variety of vena cava filters have been suggested for use, the need remains for a filter that can be temporarily installed in the vena cava for later removal, and for a filter enabling blood clots captured by it to be readily visualized by the introduction of a contrast medium. It would be particularly desirable to provide a filter assembly capable of deploying an easily removable filter element, but that may also deploy an anchoring element proximal to (that is, downstream from) the filter element, as warranted by a patient's condition. It would also be desirable to provide a filter, the center or apex of which is positioned and maintained at or near the center of the lumen, so as to improve clot filtering efficiency. Moreover, it would be desirable to provide a filter assembly enabling a contrast medium or other fluid to be injected upstream from the filter elements.

SUMMARY OF THE INVENTION

We have developed a filter assembly capable of deploying a filter element or both a filter element and an anchoring element in vessels of the body such as the vena cava and other vessels of the body, particularly in the vasculature and especially in the larger vessels. In a preferred embodiment, our filter assembly has a configuration that enables apices of these elements to remain substantially in the center of the lumen to improve filter efficiency, whether the filter assembly is deployed in its temporary or permanent configuration. For ease of explanation, the filter assembly of our invention will be described in connection with its use in the vena cava, but it will be understood that the filter assembly may be employed in various other vessels of the body.

Our filter desirably is so constructed as to enable it to deploy a distal filter element in a temporary configuration or, in a permanent configuration, to add an anchoring element. When only the filter element is deployed, the filter assembly remains attached to a tether that enables the filter to be removed from the body or repositioned in the vessel. Upon deployment of the anchoring element, the tether is detached and withdrawn, leaving the filter assembly comprising both the filter and anchoring elements in place in the vessel.

Thus, in one embodiment, the invention provides a catheter-deliverable filter assembly for deployment in a vessel of the body in alternatively a temporary configuration in which only a filter element is deployed that can be removed from or repositioned in the vessel or a permanent configuration in which an additional anchoring element is deployed which grips the walls of the vessel. The filter assembly comprises an elongated support having proximal and distal ends. Separate filter and anchoring elements are spaced axially along the support, and each element comprises a core carried by the support and a plurality of flexible, resilient wires having proximal portions attached to the core and distal portions extending outwardly distally of the core and configured to resiliently contact walls of a vessel. The wires of each element converge proximally toward their respective cores to define apices of the elements, the filter element being spaced distally of said anchoring element. The anchoring element alone includes gripping elements adapted to grip the walls of a vessel to anchor the filter assembly in the vessel.

The filter assembly in one embodiment includes a hollow flexible tether releasably attached to the distal end of the elongated support and having a tubular, distal end portion within which are resiliently confined the wires forming said anchoring element when only the distal filter element is deployed. The filter assembly desirably also includes a delivery catheter having an inner bore within which the core and wires of the filter element are received in an elastically restrained orientation to enable delivery of the filter assembly to the vessel, whereupon withdrawal of the delivery catheter enables the wires of the filter element but not the anchoring element to be deployed in the vessel.

When the filter assembly has been properly placed within the vena cava, the delivery catheter is removed to deploy the wires of the filter element, the wires of the anchoring element remaining confined within the hollow end portion of the tether. As so deployed in its temporary or tethered configuration, the filter can be withdrawn from the body easily and without significant surgical intervention.

For deployment of the filter assembly in a permanent configuration, the hollow end portion of the tether is withdrawn proximally from the anchoring element to free its wires and enable them to expand divergently from the anchoring element core to deploy within the vessel, the gripping elements carried by the anchoring element wires engaging the surface of the lumen to anchor the filter assembly in the vena cava with the apex of each element being supported by its wires substantially in the center of the vessel.

Accordingly, the invention in another embodiment comprises a method for deploying a filter in the lumen of a patient's vessel. The method comprises the following steps:

a. A filter assembly is provided which includes an elongated support having proximal and distal ends, and axially spaced filter and anchoring elements, each element comprising a core mounted coaxially to the support and having a plurality of flexible, resilient wires extending distally from its core. The anchoring element is spaced proximally from the filter element and has wires containing gripping elements for gripping the walls of a vessel. The assembly includes a delivery catheter having an inner bore within which said filter element core and wires are slidably received in an elastically restrained orientation and having a distally open end. A flexible tubular tether is carried slidably within the delivery catheter and has a hollow distal end portion releasably locked to the proximal end of the elongated support, the hollow distal end portion of the tether extending distally over and elastically restraining the wires of the anchoring element.

b. The delivery catheter is inserted into the vessel until its distal end is positioned adjacent the desired location for the filter element. The tubular tether, carrying at its distal end the elongated support together with the filter and anchoring elements, is slidable within the delivery catheter to deliver the elastically restrained filter element wires to the distal end of the catheter.

c. The delivery catheter is proximally removed to free the wires of the filter element to enable them to elastically contact the lumen of the vessel with the proximal portions of said wires converging proximally to form the apex of the filter element and with portions of the distal wire end portions of the filter element laying in line contact against and along the lumen of the vessel for a distance sufficient to substantially center said filter element apex in the lumen. If it is desired to reposition or remove the filter element, the wires of the filter element may be drawn back within the delivery catheter.

To deploy the anchoring element of the filter assembly, the method includes the step of unlocking and proximally withdrawing the hollow tether from the elongated support to thereby free the wires of the anchoring element from the hollow tether and enable them to elastically diverge into engagement with and grip the walls of the vessel to anchor the filter assembly within the vessel, the wires of the anchoring element converging proximally to form a second apex supported substantially in the center of the vessel.

Preferably, the wires of each of the filter and anchoring elements are so disposed with respect to each other as to be out of contact with each other distally of their respective apices when the filter assembly is deployed in the lumen of a vessel. At least a portion of the length of each wire, desirably a distal end portion, may be spiraled axially in the same direction (that is, either clockwise or counter-clockwise) about the axis of the elongated support to enable the wires to be readily elastically collapsed for receipt within the delivery catheter or the hollow distal end of the tether, as the case may be, the spiral orientation of the wires enabling the wires to diverge upon release from the delivery catheter or tether into contact with the walls of the vena cava without tangling of the wires with one another.

In a preferred embodiment, the elongated support is tubular and serves as an infusion tube that extends distally from the apex of the filter element to enable a contrast medium or drug or other liquid to be injected into the vena cava just distally of (that is, upstream from) the apex of the filter element so that the fluid immediately encounters any captured blood clots and enables them to be visualized or dissolved or otherwise treated, as the case may require. In this embodiment, the flexible tether is tubular and is attached at its distal end to the tubular support in fluid communication therewith to supply contrast medium or drug to the infusion tube, the proximal end of the tether being accessible for this purpose outside the body. The elongated support also may be made as a solid, preferably at least slightly flexible rod, and the flexible tether in this embodiment may deliver a contrast medium or other liquid around, rather than through, the elongated support with the liquid in any event exiting into the vessel at or upstream from the apex of the filter element.

The line contact between the distal portions of the filter element wires and the walls of the lumen serve not only to center the filter apex in the lumen, but to also substantially center the distal end of the infusion tube in the lumen, the infusion tube thus extending substantially parallel to the vessel. Such line contact also inhibits penetration of the walls of the vena cava by ends of the wire.

When only the filter element is deployed, the tether, which is sufficiently stiff as to resist collapse in the vena cava, also serves to support, center, and maintain that filter element and infusion tube in its tethered configuration within the lumen of the vena cava. The tether has a distal end portion that releasably and rigidly locks to the tubular support such that when the delivery catheter is removed, the tether will remain in place for the purpose of maintaining and centering the filter element within the vena cava and for supplying a liquid such as a contrast medium just upstream from the filter element.

The unique characteristics of the filter deployment assembly of the invention provide physicians, particularly interventional radiologists, with various options for deployment of the filter assembly in either its temporary or permanent configuration. As described in greater detail below, the tether together with the filter assembly is slidably received within the delivery catheter with the filter element wires remaining elastically confined within the delivery catheter as the filter assembly is moved within the delivery catheter. When the catheter has been appropriately positioned within the vena cava, using routine central venous access techniques, the filter assembly is slidably moved to the distal end of the delivery catheter, if it is not already there, and the delivery catheter is removed proximally, freeing the filter element wires which then elastically expand into contact with the walls of the vena cava. The resulting tethered or temporary configuration of the filter assembly enables a fluid such as a contrast medium to be injected from the hollow tether and through or around the elongated support, and also permits the filter element to be repositioned in the vessel or to be withdrawn proximally from the body, with the aid, if needed, of a catheter such as the delivery catheter that is passed over the tether to confine the previously freed wire portions within the catheter.

If desired, the entire filter assembly may be deployed in the lumen by passing it through a properly positioned delivery catheter, using a dilator or other push-rod within the catheter.

To permanently deploy the filter assembly, a flexible release rod may be inserted into the tether and passed along into contact with the lock that releasably locks the tether to the elongated support. Distal movement of the rod with respect to the tether at this point unlocks the tether from the support. Withdrawal of the thus released tether while holding the elongated support axially stationary with the release rod frees the wires of the anchoring element from the confinement of the distal end portion of the tether. Unconfined, the anchoring element wires elastically expand radially, the wires in this configuration converging at the filter core to form the apex of the permanently deployed filter. Gripping elements, such as proximally facing hooks, prongs or the like, are carried by the anchoring element wires. As the latter wires are elastically pressed against the vessel walls, the gripping elements grip the walls to anchor the filter assembly in place. The filter assembly with both elements deployed is thus left behind as a permanently deployed filter assembly as the tether is removed from the body. By "centrally disposed" or "approximately centered" or the like in connection with the position of the apex of each element within the lumen, we mean that the apex is positioned within about the central one-half, preferably the central one-third, of the diameter of the lumen.

The vena cava and other large vessels of the venous system are thin walled and are easily perforated. The wires of the filter and anchoring elements, and preferably at least those of the filter element, may terminate in enlarged ends which may be rounded or generally spheroidal, the enlarged ends inhibiting penetration of the walls of the vena cava by the distal ends of the wires.

Upon deployment of only the filter element in the vena cava, with the tubular tether attached, the proximal end portion of the tether that protrudes from the entry site of the internal jugular vein or other vessel where catheter entry was gained can be buried beneath the skin for a number of centimeters using known tunneling techniques, the wound over the entry site being closed to prevent infection. The proximal end of the tether protrudes from the skin at a location removed from the entry site and may terminate in an access element such as a controlled access hub of known design. The access element, such as a luer lock hub, provides immediate access to the tether for the purpose of delivering a contrast medium or other fluid just upstream from the filter element. If the tether is to be removed, either in the course of withdrawing the filter assembly from the vena cava or in the course of deploying the filter assembly in its permanent configuration, as discussed above, the access element is detached, the entry site is surgically opened, the buried proximal length of the tether is easily withdrawn from the subcutaneous tunnel, and the tether is then withdrawn from the vasculature.

In its tethered configuration, the filter element with its elongated support serving as an infusion tube provides excellent access to the interior of the vena cava at a location distal to or at the apex of the filter element and preferably upstream therefrom. When a fluid is injected for the purpose of visualizing a captured clot or for management of clots, it is anticipated that less fluid will be required because the fluid is concentrated at the clot location rather than being diffused in the blood flow far upstream from the filter. Moreover, use of the infusion tube for this purpose avoids the necessity of performing a costly and time consuming secondary site access procedure to utilize a separate catheter. The infusion tube may be used for the infusion of anticoagulants in clot management, for infusion of chemotherapy drugs, systemic antibiotics and for parenteral feeding, as well as enabling the collection of blood samples.

It will be understood that it is important that the wires forming the filter and anchoring elements, being bent as they are, be prevented from rotating about their respective axes. The wires commonly are quite fine, in the order of 0.005 to about 0.025 inches (about 0.13 mm to about 0.6 mm) in diameter, and it is difficult to mount the wires in bores formed in the cores in a manner preventing rotation of the wires in the bores. We have found that the wires can be easily attached to the cores in a manner that prevents their rotation, by providing a series of circumferentially spaced, axially extending bores through the cores, doubling a length of wire back upon itself to form two legs, and threading the legs distally through different, preferably adjacent, circumferentially spaced bores in the core. Each of the wire lengths, then, forms two distally-extending wires.

BRIEF DESCRIPTION OF THE DRAWING

FIG. 5 is a broken-away view in partial cross-section showing elements of the filter assembly of FIG. 1;

FIG. 6 is a broken-away cross-sectional view of a filter assembly of the invention before deployment of the anchoring element thereof.

DETAILED DESCRIPTION OF THE PREFERRED EMBODIMENT

The wires employed in both the filter and anchoring elements are flexible and resilient, and are capable of being elastically deformed from a predetermined configuration (as where the wires, unconfined by the tether or delivery catheter, are in contact with the walls of the vena cava) to another configuration (as when the wires are elastically confined within the proximal end portions of the tether and catheter) and of elastically regaining, at least in part, their predetermined configuration. The wires must be formed of a biocompatible material, of course, and may for example be of stainless steel, cobalt-chromium alloys, titanium, etc.

The filter wires may be formed of a superelastic alloy such as nitinol. Superelasticity refers to a phase transition that occurs in a superelastic alloy such as nitinol when a deforming stress is externally applied. Nitinol, a near stoichiometric alloy of nickel and titanium, as well as other superelastic alloys, (sometimes called shape memory alloys), basically exists in either of two crystallographic forms. Which form the alloy will be in depends upon several variables including ambient temperature, chemical composition and thermomechanical history of the alloy. For nitinol, austenite is the parent phase, characterized by a body centered cubic structure. Martensite is a transition phase and is characterized by a monoclinic crystalline structure. Generally, austenite will be present at a higher temperature than will martensite. As the temperature of a superelastic alloy in its austenite phase is reduced, a temperature $M_s$ at which the austenite begins to transform into martensite is reached, this temperature being referred to herein as the transformation temperature.

Filter wires that are formed of a superelastic alloy preferably are in the austenite phase at the temperature of use (body temperature) and undergo partial transformation to martensite when deformed by being radially compressed for receipt within the tether or delivery catheter. Austenite will be transformed into martensite when the alloy is deformed by an external physical stress, this phenomenon sometimes being referred to as stress-induced martensite formation. The area of the alloy that is thus deformed will remain in the martensite phase as long as the deforming force is maintained. When the stress is relieved, the deformed portion will tend to resume its original shape and in so doing will revert back to the austenite phase. This phenomenon is the basis of superelasticity.

Figure 2:
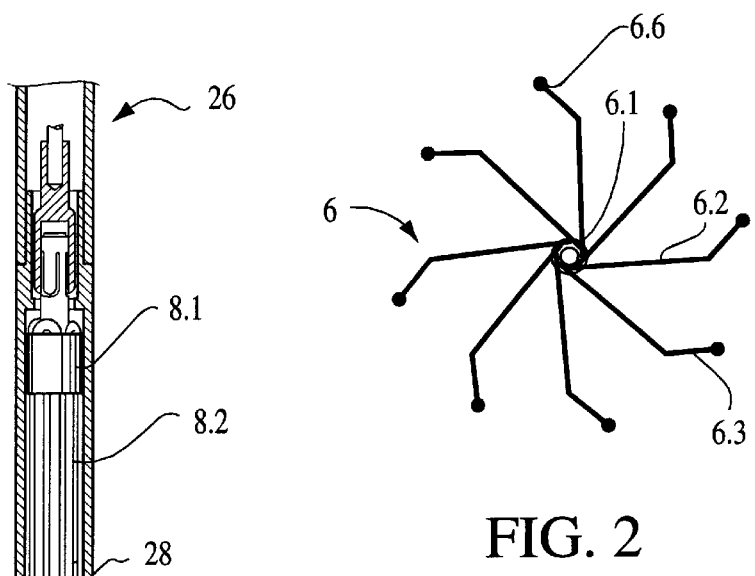
FIG. 2 is a bottom end view of the filter assembly of FIG. 1, showing the configuration of the wires.
Figure 3:
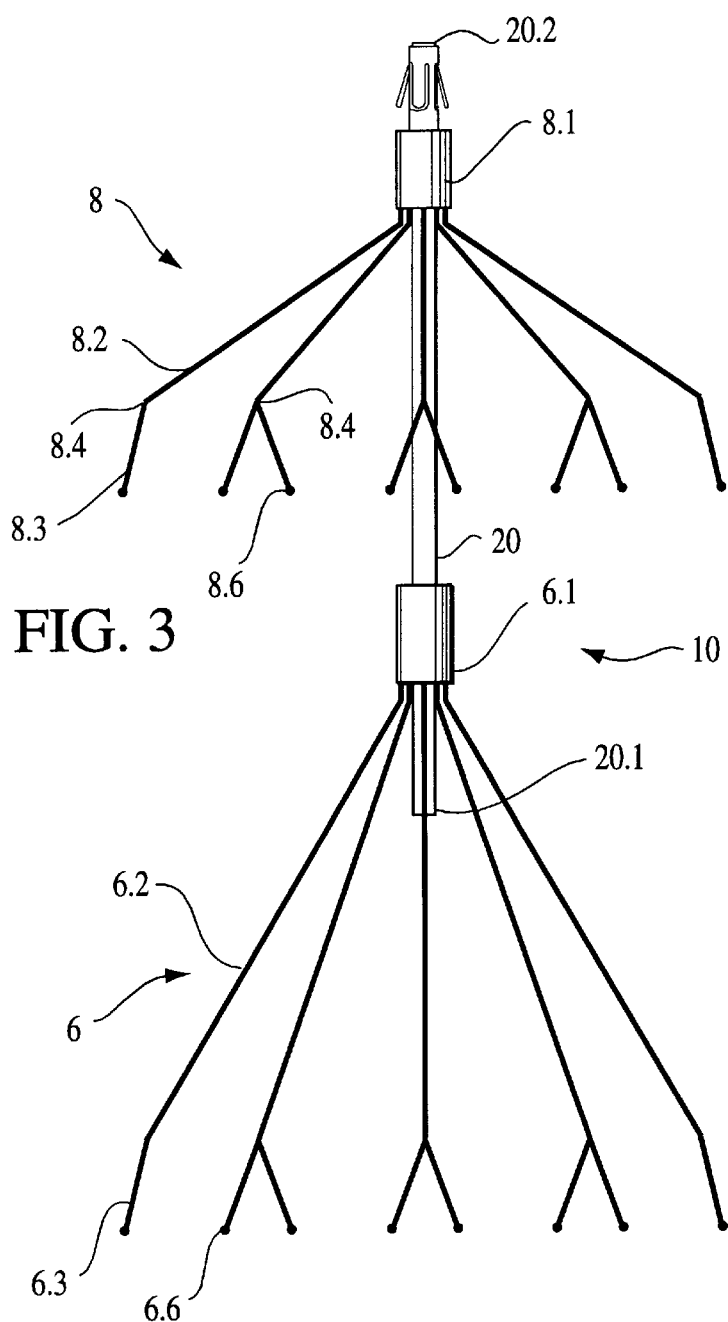
FIG. 3 is a broken-away, side view of the filter assembly of FIG. 1 with both the filter element and anchoring element wires deployed.
Figure 3A:
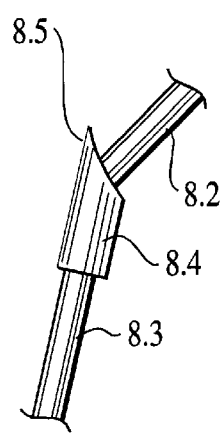
FIG. 3A is a broken-away view of a anchoring element wire with a gripping element attached.

Referring first to FIG. 3, a filter assembly of the invention is designated generally as 10 and includes an elongated, tubular support 20 having open, distal and proximal ends 20.1, 20.2, respectively. Mounted in spaced relation along the elongated support 20 are filter and anchoring elements 6, 8, respectively, each including a generally cylindrical core 6.1, 8.1 from which extends a plurality of circumferentially spaced wires 6.2, 8.2, the wires of each element extending distally and outwardly from their connections to their respective cores in desirably a generally conical configuration. Near their respective ends, the wires have sections 6.3, 8.3 bent in a slightly more distal direction to afford line contact with the vessel walls. These sections, moreover, are oriented so as to spiral slightly in the same rotational direction, as shown best in FIG. 2. The slight rotation accorded the ends 6.3 enables them to nest neatly when the wires are elastically compressed, as when they are captured in a delivery catheter.

The wires 8.2 of the proximal anchoring element 8 include along their lengths gripping elements 8.4. The gripping elements can be of any type capable of gripping to the walls of the vena cava or other vessel, and may, for example, take the form of roughened portions of the wires 8.2. Preferably, the gripping elements 8.4 are formed as small barbs having generally proximally oriented sharp ends 8.5. The barbs 8.4 may be fashioned from the end portions of hypodermic needles having an interior diameter closely receiving the wires, the barbs being crimped, welded, or otherwise fastened to the distal wire portions 8.3 to hold them in place.

To prevent the ends of the wires from penetrating the walls of the vena cava or other vessel, the wires desirably terminate distally in enlarged, bulbous or sphere-shaped ends 6.6, 8.6, which can be formed by known melting procedures.

Figure 4:
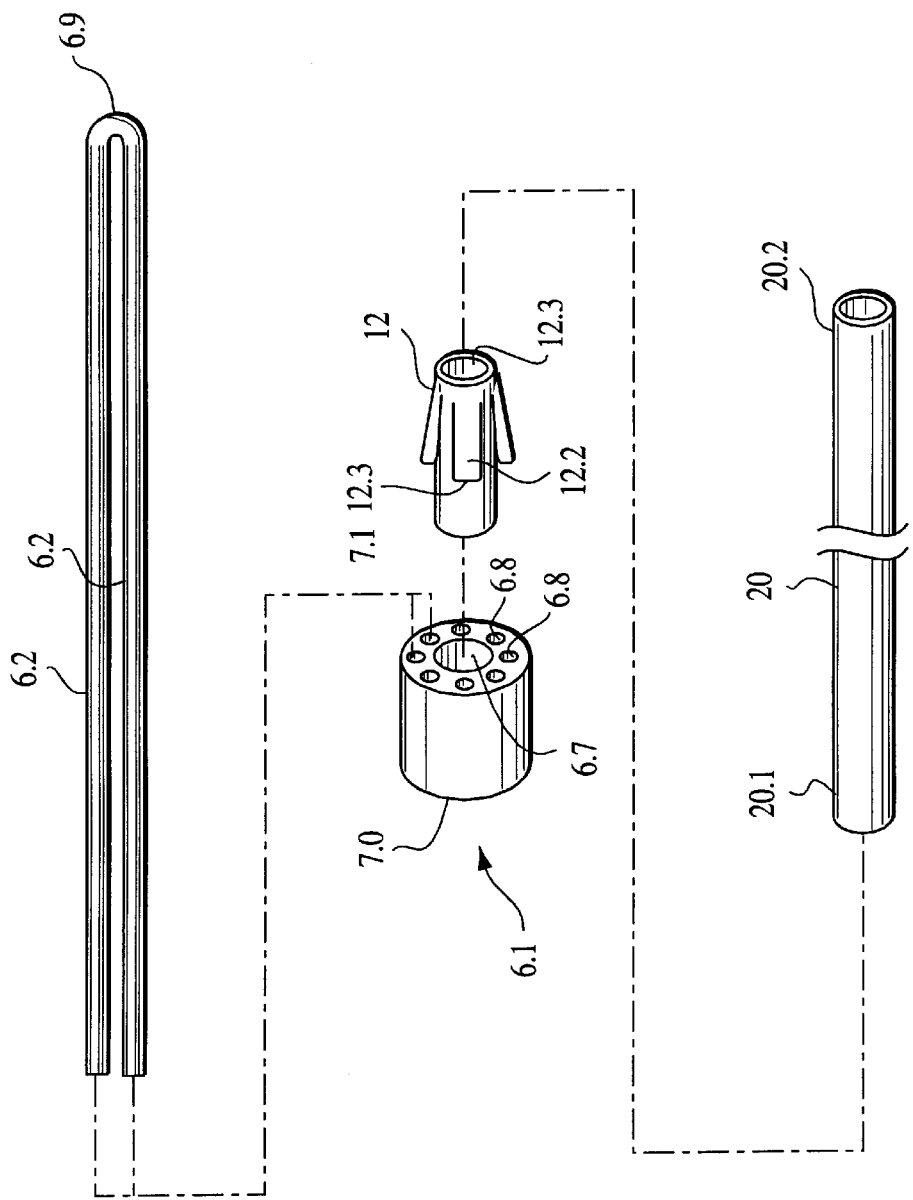
FIG. 4 is an exploded view of portions of the filter assembly of FIG. 1.

The assembly of the cores, wires and elongated support is shown best in the exploded view of FIG. 4. In this figure, the core 6.1, which may be identical to the core 8.1, is shown as being generally cylindrical in shape and having a central bore 6.7 sized to closely fit over the elongated support 20. The core may be affixed to the support 20 mechanically as by crimping, chemically through the use of adhesives, thermally as by welding, etc. A series of circumferentially spaced bores 6.8 are formed through the core parallel to its axis. We have found that the wires 6.2 can readily be affixed to the core securely and without permitting the wires to rotate about their axes by forming a pair of wires 6.2 from a single length of wire doubled back upon itself at its midpoint to form a U-shaped bend 6.9. The distal ends of the wires are received within the circumferentially spaced bores 6.8 of the core body, and preferably through adjacent bores 6.8, so that the wires protrude distally from the distal end 7.0 of the core body with the U-shaped bend 6.9 being adjacent the proximal end 7.1 of the core body. As required, the wires may be cemented, crimped, or otherwise fastened to the core to restrain any significant axial rotational movement of the wires in the bores 6.8. Axial movement of the wires relative to the cores may be prevented by subsequent heat treatment of the wires into their desired geometries.

Although the assembly of wires in the core, and mounting of the core upon the elongated support 20, has been described in connection with the filter element 6, it will be understood that the anchoring element 8 is similarly assembled and mounted on the elongated support nearer its proximal end 20.2, as shown best in FIG. 3. Desirably, the distal end 20.1 of the elongated support is slightly flared at its end as an added measure to deter the core 6.1 from escaping distally from the elongated support 20. If desired, as when femoral access to the inferior vena cava is desired, the elongated support may be made from a solid rod of plastic or other material, preferably flexible to aid in its placement in the lumen.

At its proximal end 20.2, the elongated support 20 is provided with a tubular locking member 12, perhaps best shown in FIGS. 4 and 6. The generally cylindrical locking member has an inner bore 12.3 enabling it to be snugly received on the elongated support 20, the lock 12 being securely fastened to the elongated tubular support 20 adjacent its proximal end 20.2. The latter end may be flared outwardly slightly to further deter escape of the tubular lock 12 proximally from the elongated support 20. The generally tubular lock 12 includes a plurality of circumferentially spaced, distally extending fingers 12.2, which may be simply formed by making U-shaped slits through the cylindrical walls of the tubular lock as shown, and then bending the resulting fingers outwardly slightly, as shown best in FIGS. 4 and 6. The lock 12 is made of a springy material such that the fingers 12.2, when under no radially directed stress, occupy the position shown in FIG. 6, that is, the fingers extend radially outwardly slightly from the adjacent walls of the tubular lock and terminate distally in surfaces 12.3, the function of which will be explained below. Particularly in the embodiment in which the elongated support is a solid rather than a tubular support, the connection between the tubular tether and the elongated support is sufficiently loose, or is otherwise provided with openings, so that imaging fluid or other liquid injected into the tether may exit from the distal end of the tubular tether into the vessel approximately at or slightly upstream from the apex of the filter element.

Figure 1:
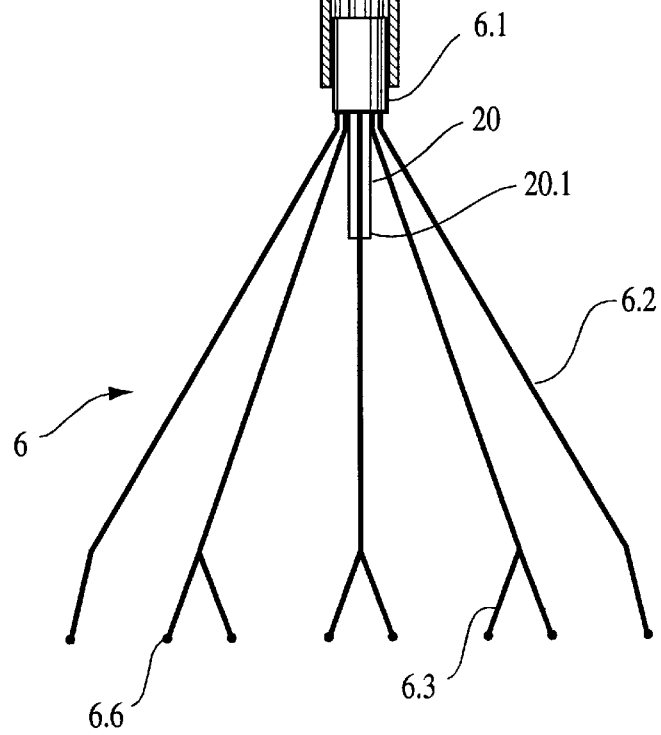
FIG. 1 is a broken-away, side view of a filter assembly of the invention with only the filter element deployed.

Referring now to FIG. 1, which shows the filter assembly of the invention with only the distal filter element 6 deployed, there is provided a tether 26, the tether including a rigid distal constraining tube portion 28 formed of metal or plastic or the like, and a long, flexible, tubular proximal portion 30. The latter may be a polymeric tube having walls supported through the use of a coiled wire insert such as that shown at 30.1 in FIG. 5, the latter being for the purpose of maintaining the tether portion 30 open and available for fluid flow as needed. The tubular distal portion 28 of the tether terminates proximally in an end portion 28.1 of reduced outer diameter, over which the distal end of the flexible tether portion is received, an adhesive or swaging procedure or the like being used to fasten these portions securely together.

Just proximally of the proximal end 9.1 of the core 8.1, the inner diameter of the rigid tether portion 28 is reduced to form a distally facing shoulder 28.2 which arrests relative proximal movement of the core 8.1 within the tether. Proceeding proximally, the inner diameter of the tether portion 28 then increases abruptly to form a proximally facing shoulder 28.3. With reference to FIG. 6, it will be noted that the fingers 12.2 of the lock, when under no radially inwardly stress, occupy the position shown in FIG. 6; that is, the fingers extend radially outwardly slightly from the adjacent walls of the tubular lock. Distal ends 12.3 of the fingers thus come into contact with the annular shoulder 28.3 of the tether so as to prevent the tether from being drawn proximally with respect to the lock 32. Although various locking mechanisms will be apparent to those skilled in the art, the locking mechanism thus described has been found to be the most reliable in operation.

Figure 7:
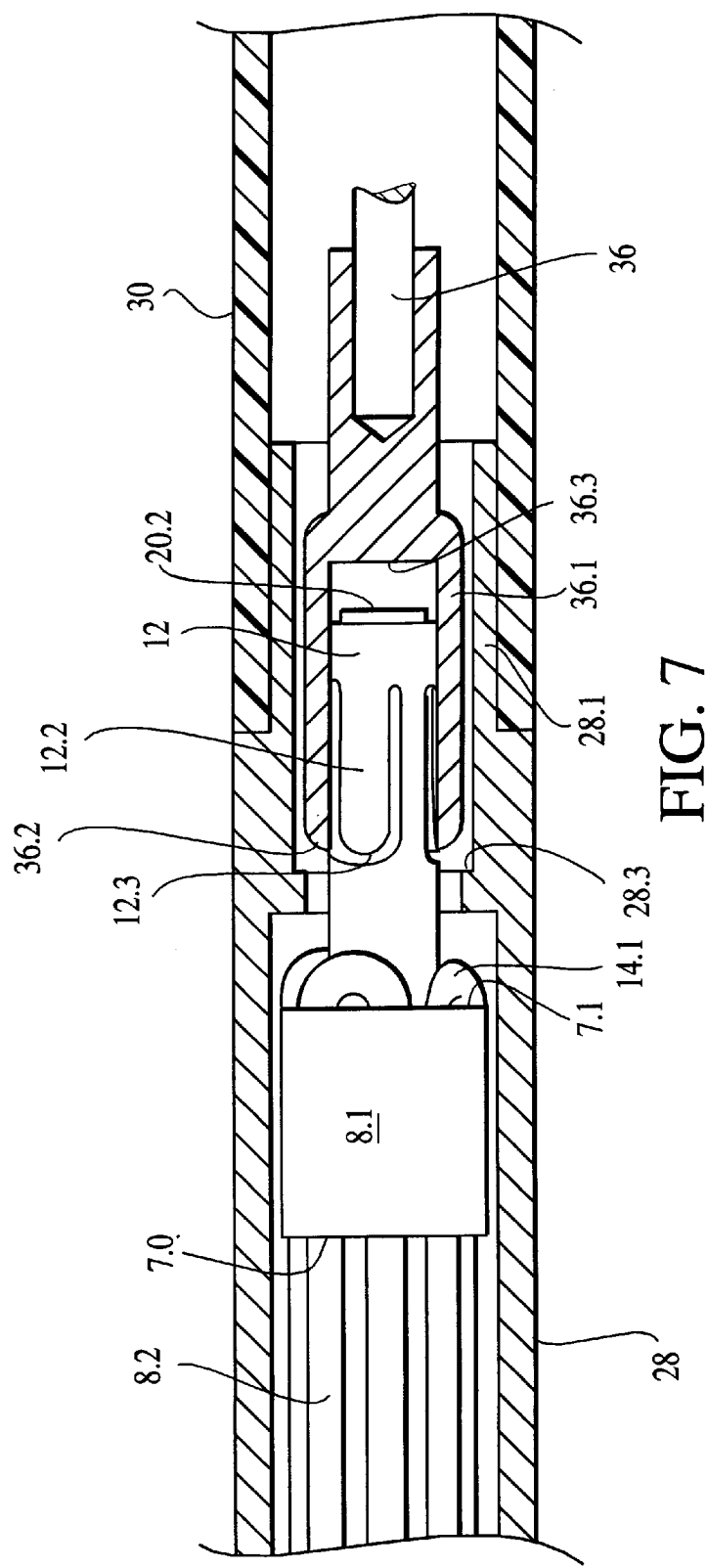
FIG. 7 is a view similar to FIG. 6 but showing the anchoring element in an early stage of deployment.

Whereas FIG. 6 shows the release rod 36 positioned within the flexible tether 30 and approaching the tubular lock, in FIG. 7 the rim 36.2 of the release rod has cammed the resilient FIGS. 32.2 inwardly and out of contact with the annular shoulder 28.3. At this point, the tether may be withdrawn proximally, that is, to the right in FIG. 7, from the lock 12 and attached core and wires, the tether being withdrawn while the release rod is held in an axially stationary position as shown so the core 8.1 and the attached wires undergo little or no axial movement with respect to the vessel walls. Proximal withdrawal of the tether portion 28 permits the wires 8.2 of the anchoring element to deploy within the vessel, the barbs 8.5 or other gripping elements encountering and gripping to the walls of the vessel to restrain downstream movement of the filter assembly. Once the tether has been withdrawn sufficiently to enable the wires 8.2 to reach full deployment, both the tether and the release rod may be removed. It will be understood that the amount of camming force needed to resiliently cam the fingers from the position shown in FIG. 6 to the position shown in FIG. 7 is not great, and as a result, the release rod 36 can easily be withdrawn proximally from contact with the fingers The locking mechanism thus described may be unlocked, accordingly, by radially compressing the fingers 32.1 so they escape from the proximally facing shoulder 28.3 of the tether. This is accomplished through the use of a flexible, elongated release rod 36 which is slidably received within the tubular tether and which carries, at its forward or distal end, a distally open, rigid tubular portion 36.1 having an outer diameter enabling it to be inserted within the proximal end 28.1 of the distal end portion of the tether, and an inner diameter enabling it to pass over the flared end 20.2 of the elongated support. The tubular portion 36.1 terminates distally in a rim 36.2 having an inner diameter which is not greater than the inner diameter of the annular shoulder 28.3 and which encounters and cams radially inwardly the fingers 32.2 so that their distal ends escape from the annular shoulder 28.3 of the tether. The distally open cavity 36.4 formed by the tubular end portion 36.1 of the release rod includes a distally facing floor 36.3 so configured as to bear against the proximal end 20.2 of the elongated support 20.

With reference again to FIG. 5, a delivery catheter 38 is employed to deliver the filter assembly within a vessel as desired. The delivery catheter 38 has an inner diameter sufficient to slidably accommodate the flexible tether 30 and the elongated support 20 together with attached cores and wires. With reference to FIGS. 1 and 5, it will be understood that the delivery catheter may be placed in the vessel so that its distal end 38.1 is positioned approximately at the desired site of deployment of the filter element 6. When the filter assembly is ready for deployment within a vessel, the assembly, with attached flexible tether, is introduced into the delivery catheter, the wires of the filter element 6 being compressed within the delivery catheter and the elastically compressed wires 8.2 of the anchoring element 8 being confined within the tubular end portion 28 of the tether. The filter assembly is advanced within the delivery catheter until the distal ends of the filter wires 6.2 are at the distal opening at the end 38.1 of the catheter, whereupon withdrawal of the delivery catheter proximally of the filter assembly releases the wires of the filter element, enabling them to expand resiliently into contact with walls of the lumen. Subsequent withdrawal of the tether, as explained above, releases the wires of the anchoring element so that they similarly expand into contact with the walls of the lumen.

When both the filter and anchoring elements are deployed within a vessel, the tubular support element 20 desirably is held substantially in the center of the vessel, with the apices of the elements similarly supported substantially in the center of the vessel. By "apex", as used herein, we mean the point (actually, the small area) of convergence of the wires of each element. The apices of each element form the center of the element defined by the wires, and the wires of one element may be aligned axially with the wires of the other element, or not, as desired, and one or both cores 6.1, 8.1, may be mounted with rotational freedom on the elongated support. For a vessel of a given diameter, the size of the elements desirably are chosen such that their distal end portions lie along and preferably in line contact with the walls of the vessel in which the filter assembly is deployed to thereby position the apices of the respective elements near the center of the vessel and to enable the gripping elements of the anchoring element to properly deploy against the walls of the vessel.

The filter assembly of the invention can thus be readily deployed in either of two configurations within the lumen of a vessel such as the inferior vena cava. The filter assembly itself can be deployed using common catheter placement techniques of the type known in the medical field. Once the end of the filter element is in place, the delivery catheter (shown at 38 in FIG. 5) is removed proximally to enable the filter element 6 to be deployed. If the patient's medical condition indicates that the filter assembly should remain permanently in the vena cava, then the tubular tether is removed as described above. While in place, however, the tether serves not only to maintain the filter element in place, centered, but also as a convenient tube for supplying an imaging fluid or other material to the infusion tube and for withdrawing blood samples from the blood stream, as needed.

While a preferred embodiment of the present invention has been described, it should be understood that various changes, adaptations and modifications may be made therein without departing from the spirit of the invention and the scope of the appended claims.

What is claimed is:

1. A filter assembly deployable in the lumen of a vessel, the filter assembly comprising an elongated support having distal and proximal ends, a core attached to the elongated support proximally of the distal end of the support and having a central axis, and a plurality of flexible, resilient wires extending distally from the core to define a filter element and terminating distally of the distal end of the support, each wire having a proximal portion attached to the core to define an apex and a distal portion extending distally from the core, and a flexible hollow tether having a distal end portion locked to the proximal end of the elongated support to enable a fluid to be ejected distally of the filter apex.

2. The filter assembly of claim 1 wherein the distal end portion of the tubular tether includes an inner lip having a proximally facing surface and said elongated support includes a portion receivable proximally of said lip within the distal end portion of the tether and bearing a latch having a distally facing surface engaging the proximally facing surface of the lip of the tether to releasably lock the tether to the elongated support.

3. The filter assembly of claim 2 wherein said latch is tubular and includes a plurality of radially resilient projections protruding radially from the latch and positioned to be cammed radially inwardly by the rigid tubular portion of said lock release.

4. The filter assembly of claim 3 wherein said radially resilient projections arise from the outer surface of the tubular latch and extend outwardly and distally, terminating distally in said distally facing surface.

5. The filter assembly of claim 2 wherein said lock release comprises a distally-open rigid tubular portion shaped to engage and cam said latch out of contact with said lip to unlock the tether from the elongated support.

6. The filter assembly of claim 1 wherein the distal end of said tether is releasably locked to the proximal end of the elongated tubular support and extends distally over and elastically confines said wires, the filter assembly including a flexible wire slidably received in said tether and carrying at its distal end a lock release for releasing the tether from the elongated support to enable the tether to be withdrawn from elastic confinement of the wires and thereby enable the wires to elastically diverge distally into contact with walls of a vessel.

7. The filter assembly of claim 1 wherein said distal portions of the wires each have a length so configured as to spiral axially in the same direction when collapsed to facilitate non-tangling release of the wires as they elastically diverge distally into contact with walls of a vessel.

8. The filter assembly of claim 1 wherein the cross-sectional area of the distal portions of the wires is less that that of the proximal wire portions to provide the distal wire portions with comparatively greater flexibility.

9. The filter assembly of claim 1 wherein said core includes a plurality of axially extending bores spaced circumferentially of the central axis, and wherein an adjacent pair of said wires comprise the legs of a U shaped wire length, the legs extending distally through adjacent ones of said axially extending bores to lock each wire to the filter core and to prevent rotation of said wires about their respective axes within said circumferentially spaced bores.

10. The filter assembly of claim 1, wherein the wires of the filter element terminate distally in enlarged ends to restrain penetration of walls of a vessel.

11. A filter assembly for deploying a filter in the lumen of a vessel, comprising
   a. an elongated support having proximal and distal ends, and axially spaced filter and anchoring elements each comprising a core mounted coaxially to the support and a plurality of flexible, resilient wires extending from the core and having proximal and distal portions, the distal portions being configured to lie against and along the walls of a vessel, the anchoring element being spaced proximally from the filter element and having wires containing gripping elements for gripping the walls of a vessel;
   b. a flexible tubular tether having a hollow distal end portion releasably locked to the proximal end of the elongated support and extending distally over and constraining the wires of said anchoring element in an elastically collapsed orientation against the elongated support;
   c. a delivery catheter having an inner bore within which said tether, elongated support and filter and anchoring elements may be slidably received, the wires of the filter element being maintained in an elastically collapsed orientation by the delivery catheter until released into contact with walls of a vessel upon proximal withdrawal of the catheter from the filter element;
   d. a flexible wire slidably receivable in said tether and bearing at its distal end a lock release for releasing the tether from the elongated support to enable the tether to be withdrawn from the anchoring element and to thereby enable the wires of the anchoring element to engage and grip the walls of the vessel.

12. A catheter-deliverable filter assembly for deploying a filter element in a vessel of the body, comprising
   an elongated support having proximal and distal ends, separate filter and anchoring elements spaced axially along said support and each comprising a core carried by the support and a plurality of flexible, resilient wires having proximal portions attached to the core and distal portions extending distally of the core and configured to expand into resilient contact with walls of a vessel, said wires converging proximally toward their respective cores to define apices of the respective elements, said filter element being spaced distally of said anchoring element, and said anchoring element alone including gripping elements carried by distal portions of said wires and adapted to grip the walls of a vessel to anchor the filter assembly in the vessel, the filter assembly including a hollow flexible tether releasably attached to the proximal end of the support and having a tubular, distal end portion within which are resilient confined the wires forming said anchoring element when only the distal filter element is deployed, said elongated support being tubular and including open distal and proximal ends to define an infusion tube extending distally from the filter element and having a proximal end in fluid communication with the hollow tether to enable a fluid to be ejected distally of the filter element.

13. A catheter-deliverable filter assembly for deploying a filter element in a vessel of the body, comprising an elongated support having proximal and distal ends, separate filter and anchoring elements spaced axially along said support and each comprising a core carried by the support and a plurality of flexible, resilient wires having proximal portions attached to the core and distal portions extending distally of the core and configured to expand into resilient contact with walls of a vessel, said wires converging proximally toward their respective cores to define apices of the respective elements, said filter element being spaced distally of said anchoring element, and said anchoring element alone including gripping elements carried by distal portions of said wires and adapted to grip the walls of a vessel to anchor the filter assembly in the vessel, the filter assembly including a hollow flexible tether releasably attached to the proximal end of the support, the distal end portion of the tether being releasably locked to said elongated support, the filter element including a flexible wire slidably received in said tether and bearing at its distal end a lock release for releasing the tether from the support to enable the tether to be withdrawn from the filter assembly.

* * * * *